US006274162B1

(12) United States Patent
Steffenino et al.

(10) Patent No.: US 6,274,162 B1
(45) Date of Patent: Aug. 14, 2001

(54) ELEGANT FILM COATING SYSTEM

(75) Inventors: Rita M. Steffenino, Green Lane; Charles F. Vesey, Hatfield; Kurt A. Fegely, Limerick; Brian D. Korchok, Lansdale; Stuart C. Porter, Hatfield, all of PA (US)

(73) Assignee: BPSI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/480,969

(22) Filed: Jan. 14, 2000

(51) Int. Cl.$^7$ ............................ A61K 47/00; A61K 9/14; A61K 9/36; A61K 9/40
(52) U.S. Cl. ................. 424/439; 424/486; 424/488; 424/479; 424/478
(58) Field of Search .................................. 424/479, 474, 424/302, 439, 486, 488, 478

(56) References Cited

U.S. PATENT DOCUMENTS

| | | |
|---|---|---|
| 2,139,866 | 12/1938 | Strouts . |
| 3,873,749 | 3/1975 | Carpenter . |
| 4,543,370 | 9/1985 | Porter . |
| 4,643,894 | 2/1987 | Porter . |
| 4,652,313 | 3/1987 | Den Boer . |
| 4,655,840 | 4/1987 | Wittwer . |
| 4,683,256 | 7/1987 | Porter . |
| 4,702,919 | 10/1987 | Kitamori . |
| 4,713,248 | 12/1987 | Kjorn . |
| 4,725,441 | 2/1988 | Porter . |
| 4,750,938 | 6/1988 | Cottrell . |
| 4,786,506 | 11/1988 | Fontanelli . |
| 4,816,259 | 3/1989 | Matthews . |
| 4,820,524 | 4/1989 | Berta . |
| 4,828,841 | 5/1989 | Porter . |
| 4,892,766 | 1/1990 | Jones . |
| 5,017,383 | 5/1991 | Ozawa . |
| 5,035,896 | 7/1991 | Apfel . |
| 5,104,674 | 4/1992 | Chen . |
| 5,114,720 | 5/1992 | Littell . |
| 5,146,730 | 9/1992 | Sadek . |
| 5,248,516 | 9/1993 | Wheatley . |
| 5,258,436 | 11/1993 | Wheatley . |
| 5,417,982 | 5/1995 | Modi . |
| 5,445,829 | 8/1995 | Paradissis . |
| 5,456,745 | 10/1995 | Roreger . |
| 5,470,581 | * 11/1995 | Grillo ................................. 424/479 |
| 5,607,697 | 3/1997 | Alkire . |
| 5,641,536 | 6/1997 | Lech . |
| 5,656,291 | 8/1997 | Olsson . |
| 5,658,589 | 8/1997 | Parekh . |
| 5,683,717 | 11/1997 | Shen . |
| 5,750,145 | 5/1998 | Patell . |
| 5,750,148 | 5/1998 | Maruyama . |
| 5,756,140 | * 5/1998 | Shoop et al. ...................... 426/302 |
| 5,770,225 | 6/1998 | Parekh . |
| 5,789,014 | 8/1998 | Maruyama . |
| 5,834,022 | 11/1998 | Amidon . |
| 5,837,291 | 11/1998 | Maruyama . |
| 5,853,756 | 12/1998 | Mody . |
| 5,869,094 | 2/1999 | Van Egmond . |
| 5,882,715 | 3/1999 | Nielsen . |
| 5,885,617 | * 3/1999 | Jordan ................................ 424/474 |
| 6,077,540 | 6/2000 | Daher . |

FOREIGN PATENT DOCUMENTS

| | | |
|---|---|---|
| WO 97/09967 | 3/1997 | (WO) . |
| WO 99/33924 | 7/1999 | (WO) . |

* cited by examiner

Primary Examiner—Thurman K. Page
Assistant Examiner—Blessing Fubara
(74) Attorney, Agent, or Firm—John F. A. Earley; John F. A. Earley, III; Harding, Earley, Follmer & Frailey

(57) ABSTRACT

A dry film coating composition for forming a coating suspension for film coating pharmaceuticals, food, confectionery forms, agricultural seeds, and the like, comprises (1) a primary film former, the primary film former comprising low bloom strength gelatin, or hydroxyethyl cellulose, or a combination thereof, and (2) a secondary film former, or a plasticizer, or a surfactant, or a glidant, or a suspension aid, or a colorant, or a flavorant, or a combination thereof.

81 Claims, No Drawings

ELEGANT FILM COATING SYSTEM

BACKGROUND OF THE INVENTION

1. Field of the Invention

This invention relates to the field of aqueous film coating of pharmaceutical, food, confectionery, and agricultural products, and is specifically concerned with providing film coatings having an elegant, extremely glossy, and smooth appearance.

2. Description of the Prior Art

Coating of pharmaceutical dosage forms is well known in the industry. Film coating systems that impart a finished tablet gloss also are known. Cellulosic polymers, maltodextrin, and other polymers have all been used in coatings for substrates such as pharmaceutical tablets, and to some degree impart a desired "coated tablet" appearance or gloss to the pharmaceutical tablets. For example, such coatings made from coating compositions manufactured by Colorcon, of West Point, Pa., and disclosed in Colorcon U.S. Pat. Nos. 4,543,370, 4,683,256, 4,643,894, 4,725,441, 4,828,841, and 5,470,581, Colorcon U.S. patent application Ser. No. 08/778,944, and Colorcon U.S. patent application Ser. No. 08/466,939, all of said patents and said patent applications being incorporated herein by reference, have proven especially effective when used on pharmaceutical tablets.

However, such coatings, especially clear coatings void of pigments, sometimes suffer from "frost" (a white frost-like haze imparted on the tablet surface) when coated at high weight gains for a gloss coat, such as greater than 1.0% weight gain, onto pharmaceutical tablets and the like.

In Berta U.S. Pat. No. 4,820,524, a method of coating a caplet by dipping individual ends of a caplet into a gelatinous solution is disclosed, in which gelatin of bloom strength in the range of 150–270 is used, to produce a shiny film having a thickness from 5–40 mils. Berta U.S. Pat. No. 4,820,524 also discloses a failed attempt to replicate the shine obtained by dipping by spray-coating the caplets in a coating pan with a gelatin system.

Sadek et al. U.S. Pat. No. 5,146,730 discloses a method of coating a tablet by enrobing the tablet in a gelatin coating by application of respective layers of elastic gelatin film to opposite sides of the tablet. Sadek et al. U.S. Pat. No. 5,146,730 discloses that it is essential to use gelatin with bloom values in the range of 120 to 250 to produce the desired film elasticity and adhesion characteristics.

Shen U.S. Pat. No. 5,683,717 discloses a method of spray-coating substrates with a gelatin solution consisting essentially of blooming gelatin (275 bloom), a plasticizer (which is triacetin), a surface-active agent, water, and optionally a coloring agent. The solution is heated and maintained at elevated temperatures during coating, and non-typical conditions are employed in spray-coating (an inlet temperature of 40° C. or less and an outlet temperature of 20° C. or less) to produce the desired effect.

Becker U.S. Pat. No. 5,114,720 discloses a method for coating previously coated tablets with a solution consisting essentially of only a low bloom gelatin (from pork, calfskin or bone) and water for the purpose of imparting a low coefficient of friction, and thus an increased slipperiness and swallowability to the tablet. There is no mention of improved gloss or smoothness.

Johnson et al. U.S. Pat. No. 4,931,286 discloses a high gloss pharmaceutical tablet with an outermost coating of sodium carboxymethylcellulose and a polyethylene glycol plasticizer wherein the outermost coating is applied from a water solution by spray-coating. However, such a coated tablet has a hazy appearance.

SUMMARY OF THE INVENTION

It is an object of the invention to provide a film coating that possesses an elegant, extremely glossy, and smooth appearance.

Another object of the invention is to provide a film coating that does not have a frost-like haze.

Another object of the invention is to provide a film coating from a film coating suspension that may be spray-coated onto tablets and the like at high weight gains substantially higher than 1.0% to produce film coatings having an exceptional shine and smoothness comparable to coatings produced by gel-dipping or enrobing and/or sugar-coating.

Another object of the invention is to provide a film coating from a film coating suspension that may be spray-coated onto tablets and the like using coating conditions typical to traditional spray-coating equipment.

These and other objects are accomplished by our invention, which is described below.

Our inventive dry film coating composition disclosed herein is mixed into water to create an aqueous coating suspension which is spray-coated onto pharmaceutical tablets, producing a smooth and glossy appearance similar to currently marketed gel-dipped, enrobed or sugar-coated medicinal forms, which heretofore has not been obtained, or believed to be obtainable, by spray-coating.

An added benefit to the present invention is that the inventive coating may be formed by spray-coating at weight gains substantially higher than 1% (by dry weight basis) to produce a similar coating thickness as currently commercial gel-dipped or enrobed products, without creating a frost-like or hazy appearance in the coating.

Because the coating of the present invention may be applied to tablets and the like by using traditional spray-coating equipment and room temperature mixing conditions, it represents a substantial time-savings in processing over traditional gel-dipping or sugar- coating processes, which are well-known to be lengthy processes. Further, because the coating of the invention may be applied to tablets and the like by using room temperature mixing conditions and spray- coating conditions typical to traditional spray-coating equipment, application of the film coating is easier than application of a film coating using elevated temperature mixing conditions and non-traditional spray-coating conditions such as those disclosed in Shen U.S. Pat. No. 5,683,717.

If desired, the inventive dry film coating composition may be mixed into water to create an aqueous coating suspension that may be used for dipping or enrobing substrates, such as pharmaceutical substrates, food, confectionery pieces, agricultural seeds, and the like.

DETAILED DESCRIPTION OF THE INVENTION

In accordance with the invention, our dry film coating composition for use in forming a coating suspension for film coating pharmaceuticals, food, confectionery forms, agricultural seeds, and the like, comprises gelatin and/or hydroxyethyl cellulose (HEC), and one or more of the following components: a secondary film former(s), a plasticizer(s), a surfactant(s), a glidant(s), a suspension aid(s), a colorant(s), and/or a flavorant(s).

In accordance with the invention, a method of coating substrates such as pharmaceutical tablets, food, confectionery forms, agricultural seed, and the like, comprises mixing gelatin and/or HEC into water to form our inventive aqueous coating suspension, applying the inventive coating suspension onto said substrates to form a film coating on said substrates, and drying the film coating on said substrates. Optionally, but preferably, one or more of the following components may be mixed into water with the gelatin and/or HEC to form the inventive coating suspension: a secondary film former(s), a plasticizer(s), a surfactant(s), a glidant(s), a suspension aid(s), a colorant(s), and/or a flavorant (s).

Our invention also includes the film coating formed on said substrates, the coated substrates, and the methods of making the dry film coating composition and of making our coating suspension.

The film former of the coating is hydroxyethyl cellulose (HEC), or low bloom strength, non-gelling gelatin (preferably, fish gelatin), or combinations thereof.

The secondary film former may be sodium alginate, sodium carboxymethylcellulose (NaCMC), pectin, gelatin, propylene glycol alginate, methylcellulose, polydextrose, polyvinylpyrrolidone, or combinations thereof.

The plasticizer may be glycerin, maltitol solution, propylene glycol, polyethylene glycol, triethyl citrate, glyceryl triacetate, or any other material of similar plasticizing ability, or combinations thereof.

The surfactant may be soya lecithin, sodium lauryl sulfate, polysorbate 80, or polyoxyethylene polyoxypropylene block copolymers, or combinations thereof.

The glidant may be talc, colloidal silicon dioxide, or stearic acid, or combinations thereof.

The suspension aid may be xanthan gum, propylene glycol alginate, or pectin, or combinations thereof.

The colorants may be FD&C and D&C lakes, titanium dioxide, iron oxides, natural pigments, or dyes approved for ingestion by the U.S. Federal Drug Administration, or combinations thereof.

The flavorant(s), which is used primarily for taste- and/or odor-masking, may be vanillin, sodium citrate, citric acid, mint, orange, lemon oil, or any other pharmaceutically approved flavorant or tastemasking agent, and combinations thereof. Vanillin and citric acid are preferred.

The ranges for each component of the dry coating composition are as follows, by weight:

| COMPONENT | PREFERRED RANGES | MORE PREFERRED RANGES |
|---|---|---|
| gelatin and/or HEC | 45–90% | 45–75% |
| secondary film former | 0–50% | 5–45% |
| plasticizer | 0–30% | 1–15% |
| surfactant | 0–20% | 1–10% |
| glidant | 0–13% | 0.5–5% |
| suspension aid | 0–15% | 2–12% |
| colorant | 0–27% | 0–16% |
| flavorant | 0–12% | 1–6% |

The most preferred ranges for the fish gelatin and/or HEC is 50–65% by weight of the dry film coating composition, the most preferred ranges for the secondary film former are 20–40% by weight of the dry film coating composition, and the most preferred ranges for the plasticizer are 4–10% by weight of the dry film coating composition.

EXAMPLES

We now turn to the examples of the invention, all ingredients being by weight.

The following examples of the invention all disclose formulations which may be mixed into ambient temperature water to form an aqueous coating suspension effective to coat pharmaceutical tablets, food and confectionery pieces, and agricultural seeds. Seeds are advantageously coated to meet various needs, such as color coating for identification purposes, adhesion of various additives, (e.g., pest control agents and inocula), prevention of handling damage, and facilitating the use of mechanical planting equipment. The coated forms of these examples include, but are not limited to, medicinal tablets such as aspirin tablets, acetaminophen caplets and ibuprofen tablets, vitamin tablets, and placebos, agricultural seeds and food substrates, such as chewing gum balls, candy pieces, and breakfast cereals.

Example 1

A formulation for the present inventive dry coating composition is the following:

| Component | Percent | grams |
|---|---|---|
| Byco M Spray-Dried Hydrolyzed Fish Gelatin | 53.5 | 53.5 |
| NaCMC | 25.0 | 25.0 |
| Soya Lecithin | 7.5 | 7.5 |
| PGA | 10.0 | 10.0 |
| Citric Acid Monohydrate | 2.0 | 2.0 |
| Vanillin | 2.0 | 2.0 |
|  | 100.0 | 100.0 |

Byco Spray-dried Hydrolyzed Fish Gelatin from Croda Colloids is a cold-water soluble, non-gelling gelatin derived from fish sources, and is the film former. NaCMC is Sodium Carboxy methyl Cellulose from tonhello, and is the secondary film former. Soya Lecithin (surfactant) is Alcolec F-100 from American Lecithin. PGA (suspension aid) is Propylene Glycol Alginate, Protanal Ester SD-LB from Pronova Biopolymer a.s. Citric Acid Monohydrate (ADM) and Vanillin (Rhodia) are flavorants.

The coating suspension is prepared by weighing all ingredients into a suitable-sized food processor/blender and blending for 5 minutes until a homogeneous mixture is produced. The ingredients of this formulation are all dry powders, but for purposes of clarification and in examples to follow, if any liquid ingredients are present in the formula, they are added after the initial blending of dry ingredients, and blending is then continued for an additional 5 minutes after all liquid has been introduced. Optionally, as batch sizes increase, blenders such as a P.K. blender, may be used. Blending of the aforementioned formulation also may be achieved by processing ingredients into a granular form to produce a non-dusting granular coating composition by the following methods: wet massing, fluid bed granulation, spray granulation and dry compaction, roller compaction or slugging.

Fifteen grams of the blended mixture is dispersed into 285.0 grams of ambient temperature water to make an aqueous coating suspension having a 5.0% solids content. The water is weighed into a vessel with a diameter approximately equal to the depth of the final suspension. A low sheer mixer, preferably having a mixing blade with a diameter approximately ⅓ the diameter of the mixing vessel, is lowered into the water and turned on to create a vortex from the edge of the vessel down to just above the mixing blade to prevent entrapment of air. The 15 grams of dry film coating composition is added to the vortex at a rate where there is no excessive build up of dry powder. The speed and depth of the mixing blade is adjusted to avoid air being drawn into the suspension so as to avoid foaming. The suspension is stirred for 45 minutes and is then ready for spraying onto substrates like pharmaceutical tablets.

The viscosity of this suspension ranges from 80 cP –90 cP, as measured by Brookfield Rotational Viscometer Model DV-II+, spindle 1, 20 rpm, setting S-61. A mixed substrate charge of 200 grams of ⅜" standard convex placebos and 100 grams of 5 grain aspirin cores of similar diameter, previously coated with a theoretical 3% weight gain of a pigmented film coating made from an Opadry® II coating composition, formula Y-22-15118 (red), manufactured by Colorcon, West Point, Pa. and made in accordance with the disclosure in Colorcon U.S. Pat. No. 5,630,871, which is incorporated herein by reference, is spray-coated with the inventive aqueous coating suspension in an Aeromatic Strea-1 fluidized bed coater with a 1.1 mm fluid nozzle. The coating parameters are: inlet temperature 50° C., atomizing air 2 bar, feed rate 5 grams/minute. A theoretical weight gain of 5.0% is applied to the tablets, and the coated tablets are smooth, non-tacky and extremely glossy with no evidence of frost or haze in the coating. The coated tablets are slick to the touch and are easily swallowed.

Although gloss is typically and easily assessed by visual comparison of one finished product to another, the degree of coated tablet gloss is measured by Tricor Systems Gloss Analysis System Model 801A, used widely in industry to measure luster and sheen on automotive surfaces, on vinyl and in paints. This system measures the specular component of light reflecting off the samples, allowing for the measurement of gloss regardless of the shape, texture or color of the samples. All gloss measurements are directly traceable to a gloss reference standard, which is used to calibrate the instrument daily. The gloss reading attained for the coating of this specific example was 207 gloss units (g.u.). Typical gloss readings attained for standard commercially available gel-dipped or enrobed tablets range from 200 to 240 gloss units (g.u.). Gloss readings for standard commercially available sugar-coated medicaments range from 177 to 209 g.u.

Example 2

A coating mixture having the following formula is made using the procedure of Example 1:

| Component | Percent | grams |
|---|---|---|
| Hydroxy Ethyl Cellulose (HEC) | 66.0 | 66.0 |
| Polyvinylpyrrolidone (PVP) | 25.0 | 25.0 |
| Maltisweet 3145 | 5.0 | 5.0 |
| Citric Acid Monohydrate | 2.0 | 2.0 |
| Polyoxomer 188 | 2.0 | 2.0 |
| | 100.0 | 100.0 |

HEC is the film former of the composition and is Tylose supplied by Clariant. PVP is the secondary film former and is Kollidon 30 supplied by BASF. Maltisweet 3145 is maltitol solution manufactured by SPI Polyols and is the plasticizer. Polyoxomer 188 is Pluronic F68NF (surfactant), and is supplied by BASF.

The coating suspension using the coating mixture of this example is made using the procedure of Example 1, and 300 grams of ibuprofen tablets (200mg), previously coated at a 4.0% weight gain with a coating made from an Opadry® II coating composition, formula 49913354 (orange), manufactured by Colorcon and made in accordance with the disclosure in Colorcon U.S. Pat. No. 5,630,871, are spray-coated with the coating suspension of this example using the procedure of Example 1. A 5.0% weight gain is applied to the tablets, and the resultant tablets are smooth, non-tacky, and highly glossy. Gloss measurement yielded gloss units of 218.

Example 3

A coating suspension is prepared having the same formula as in Example 2, and 300 grams of 10mm deep convex aspirin cores, previously coated at a 4.0% weight gain with a coating made from an Opadry® AMB coating composition (light orange) manufactured by Colorcon, and made in accordance with the disclosure in Colorcon U.S patent application Ser. No. 08/466,939, are spray-coated with the coating suspension of this example using the procedure of Example 1. A 5.0% weight gain is applied to the cores, and the finished product is smooth, non-tacky, and yielded a gloss measurement of 215 g.u.

Example 4

A coating suspension is prepared having the same formula as in Example 2, except that Polyoxomer 237 (Pluronic F87) is substituted for Polyoxomer 188 (Pluronic F68NF) in the formulation at the same percentages, and 300 grams of 11 mm extra deep convex placebos, previously coated using the opadry® II coating composition mentioned in Example 1, are spray-coated with the coating suspension of this example using the procedure of Example 1. A 3.0% weight gain is applied, and the resultant tablets are very smooth, non-tacky, and very shiny with a gloss measurement of 196 g.u.

Example 5

A dry coating composition having the following formula is made using the procedure of Example 1:

| Component | Percent | grams |
|---|---|---|
| Hydroxy Ethyl Cellulose (HEC) | 70.0 | 70.0 |
| Polyvinylpyrrolidone (PVP) | 30.0 | 30.0 |
| | 100.0 | 100.0 |

A coating suspension is prepared using the coating composition of this example and the procedure of Example 1, and 300 grams of placebo tablets, which have been previously coated as in Example 1, are spray-coated with the inventive coating suspension of this example using the procedure of Example 1.

Example 6

A dry coating composition having the following formula is made using the procedure of Example 1:

| Component | Percent | grams |
|---|---|---|
| Byco M Spray-Dried Hydrolyzed Fish Gelatin | 53.5 | 107.0 |
| NaCMC | 25.5 | 51.0 |
| Soya Lecithin | 5.0 | 10.0 |

-continued

| Component | Percent | grams |
| --- | --- | --- |
| PGA | 10.0 | 20.0 |
| Citric Acid Monohydrate | 2.0 | 4.0 |
| Vanillin | 2.0 | 4.0 |
| Xanthan Gum | 1.0 | 2.0 |
| Polysorbate 80 | 1.0 | 2.0 |
| | 100.0 | 200.0 |

Xanthan Gum is Xantural 180 supplied by Monsanto and is functioning as a further suspension aid for the formulation, and Polysorbate 80, of vegetable source, supplied by Cesalpina, is functioning as a further surfactant in the formula.

150 grams of the dry coating composition is dispersed in 2850 grams of ambient water using the procedure of Example 1 and stirred for 45 minutes to create an aqueous coating suspension having a 5.0%

| Component | Percent | grams |
| --- | --- | --- |
| Byco M Spray-Dried Hydrolyzed Fish Gelatin | 58.5 | 58.5 |
| NaCMC | 30.0 | 30.0 |
| Soya Lecithin | 7.5 | 7.5 |
| Citric Acid Monohydrate | 2.0 | 2.0 |
| Vanillin | 2.0 | 2.0 |
| | 100.0 | 100.0 |

50 grams of the dry coating composition is dispersed in 950 grams of ambient water using the procedure of Example 1 to create an aqueous coating suspension having a 5.0% solids content.

A 1.0 kilogram charge of multivitamin tablets, which have been previously coated with a coating made from a pigmented Opadry® NS coating composition, Y-41-15146 (red), manufactured by Colorcon and disclosed in U.S. patent application Ser. No. 08/778,944, is loaded into a 12" O'Hara Labcoat I coating pan with 4 mixing baffles and 6 anti-slide bars. The aqueous coating suspension is sprayed onto the tablet bed using 1 Spraying System Gun, ⅛ VAU SS and a Masterflex digital console peristaltic pump with 1 7518-02 pumphead. During the coating procedure, the atomizing air is 20 psi, pattern air is 25 psi, inlet air temperature is 74° C., outlet air is 50° C., the tablet bed temperature is at 35° C., the pan speed is 18–20 rpm, the coating liquid feed rate is 12 g/min, and the total coating time is 1 hr and 20 minutes. A solids content. The suspension viscosity is 124 cP.

A 3.0 kilogram charge of mixed tablets consisting of 2.0 kg of ⅜" standard convex placebos and 1.0 kg of 5 grain aspirin cores of similar diameter, which have been previously coated at a 3.5% weight gain with a coating made from a pigmented Opadry® II coating composition manufactured by Colorcon, is loaded into a 15" O'Hara Labcoat I coating pan with 4 mixing baffles and 6 anti-slide bars. The aqueous coating suspension is sprayed onto the tablet bed using 1 Spraying System Gun, ⅛ VAU SS and a Masterflex digital console peristaltic pump with 1 7518-02 pumphead. During the coating procedure, the atomizing air is 25 psi, pattern air is 30 psi, inlet air temperature is 74° C., outlet air is 50C, the tablet bed temperature is at 40° C., the pan speed is 16 rpm, the coating liquid feed rate is 20 g/min, and the total coating time is 2 hrs and 34 minutes. A theoretical 5.0% dry coating weight gain is applied to the tablet charge, producing very smooth, non-tacky, very shiny coated tablets registering 211 g.u.

Example 7

A dry coating composition having the following formula is made using the procedure of Example 1: theoretical 5.0% dry coating weight gain is applied to the tablets, producing very smooth, non-tacky, very shiny coated vitamin tablets with a slick feel registering 235 g.u.

Example 8

The coating suspension is made as in Example 7, and uncoated multivitamin tablets are spray-coated using the coating procedure of Example 7. Gloss units attained were 220 g.u.

The following Examples 9 to 31, which show different formulations of the dry film coating composition of the invention, further illustrate the invention. In each Example 9 to 31, a dry film composition is made and is used for coating using the procedures and substrates described in Example 1. Alternatively, the individual ingredients of each formulation may be mixed directly into water to form the coating suspension.

Example 9

| Component | Percent | grams |
| --- | --- | --- |
| HEC | 90.0 | 90.0 |
| PEG 400 | 10.0 | 10.0 |
| | 100.0 | 100.0 |

PEG 400 is Polyethylene Glycol 400 from Clariant and functions as a plasticizer.

Example 10

| Component | Percent | grams |
| --- | --- | --- |
| HEC | 90.0 | 90.0 |
| Glycerin | 10.0 | 10.0 |
| | 100.0 | 100.0 |

Glycerin is manufactured by Dow Chemical and functions as a plasticizer.

Example 11

| Component | Percent | grams |
| --- | --- | --- |
| Fish Gelatin | 90.0 | 90.0 |
| Propylene Glycol | 10.0 | 10.0 |
| | 100.0 | 100.0 |

Propylene Glycol is supplied by Dow Chemical and functions as a plasticizer. Fish Gelatin is supplied by Norland Products Inc. and is the film former.

Example 12

| Component | Percent | grams |
|---|---|---|
| Fish Gelatin | 90.0 | 90.0 |
| Triethyl Citrate | 10.0 | 10.0 |
| | 100.0 | 100.0 |

Triethyl citrate is supplied by Morflex and functions as a plasticizer.

Example 13

| Component | Percent | grams |
|---|---|---|
| HEC | 61.0 | 61.0 |
| PVP | 25.0 | 25.0 |
| Lycasin | 5.0 | 5.0 |
| Citric Acid Monohydrate | 2.0 | 2.0 |
| Pluronic F68 | 2.0 | 2.0 |
| PEG 3000 | 5.0 | 5.0 |
| | 100.0 | 100.0 |

Lycasin is maltitol solution supplied by Roquette and functions as a plasticizer in combination with PEG 3000 which is Polyethylene Glycol 3000 from Clariant.

Example 14

| Component | Percent | grams |
|---|---|---|
| Spray Dried Hydrolyzed Fish Gelatin | 58.5 | 58.5 |
| NaCMC | 30.0 | 30.0 |
| Soya Lecithin | 7.5 | 7.5 |
| Natural Special Compound | 2.0 | 2.0 |
| Citric Acid Monohydrate | 2.0 | 2.0 |
| | 100.0 | 100.0 |

Natural Special Compound is a taste/odor-masking compound supplied by Firmenich.

Example 15

| Component | Percent | grams |
|---|---|---|
| HEC | 61.0 | 61.0 |
| PVP | 20.0 | 20.0 |
| Spray Dried Hydrolyzed Fish Gelatin | 10.0 | 10.0 |
| Lycasin | 5.0 | 5.0 |
| Citric Acid Monohydrate | 2.0 | 2.0 |
| Pluronic F68 | 2.0 | 2.0 |
| | 100.0 | 100.0 |

Example 16

| Component | Percent | grams |
|---|---|---|
| Spray Dried Hydrolyzed Fish Gelatin | 76.0 | 76.0 |
| HEC | 10.0 | 10.0 |
| Glycerin | 5.0 | 5.0 |
| Propylene Glycol | 5.0 | 5.0 |
| Soya Lecithin | 2.0 | 2.0 |
| Pluronic F87 | 2.0 | 2.0 |
| | 100.0 | 100.0 |

Example 17

| Component | Percent | grams |
|---|---|---|
| Spray Dried Hydrolyzed Fish Gelatin | 45.0 | 45.0 |
| Sodium Alginate | 45.0 | 45.0 |
| Lycasin | 5.0 | 5.0 |
| Peg 3000 | 5.0 | 5.0 |
| | 100.0 | 100.0 |

Sodium Alginate is Keltone LVCR from Monsanto and functions as a secondary film former.

Example 18

| Component | Percent | grams |
|---|---|---|
| HEC | 64.0 | 64.0 |
| PVP | 25.0 | 25.0 |
| Lycasin | 5.0 | 5.0 |
| Natural Lemon | 2.0 | 2.0 |
| Genu Pectin | 2.0 | 2.0 |
| Pluronic F87 | 2.0 | 2.0 |
| | 100.0 | 100.0 |

Genu Pectin is supplied by Hercules and is a suspending agent in the formula. Natural Lemon is supplied by Firmenich, and is a flavorant.

Example 19

| Component | Percent | grams |
|---|---|---|
| Byco M Spray Dried Hydrolyzed Fish Gelatin | 48.5 | 48.5 |
| Genu Pectin | 37.5 | 37.5 |
| Triacetin | 5.0 | 5.0 |
| Soya Lecithin | 5.0 | 5.0 |
| Citric Acid Monohydrate | 2.0 | 2.0 |
| Vanillin | 2.0 | 2.0 |
| | 100.0 | 100.0 |

Genu Pectin is the secondary film former of the formula. Triacetin is glyceryl triacetate supplied by Eastman, and functions as the plasticizer.

Example 20

| Component | Percent | grams |
| --- | --- | --- |
| HEC | 65.5 | 65.5 |
| PVP | 25.0 | 25.0 |
| Lycasin | 5.0 | 5.0 |
| Pluronic F87 | 2.0 | 2.0 |
| Citric Acid Monohydrate | 2.0 | 2.0 |
| Colloidal Silicon Dioxide | 0.5 | 0.5 |
|  | 100.0 | 100.0 |

Colloidal Silicon Dioxide is Cabosil supplied by Cabot and is the plidant.

Example 21

| Component | Percent | grams |
| --- | --- | --- |
| Byco M Spray Dried Hydrolyzed Fish Gelatin | 50.0 | 50.0 |
| Methylcellulose | 50.0 | 50.0 |
|  | 100.0 | 100.0 |

Methylcellulose is Metalose SM15 from Shinetsu and is the secondary film former of the formula.

Example 22

| Component | Percent | grams |
| --- | --- | --- |
| HEC | 61.0 | 61.0 |
| PVP | 25.0 | 25.0 |
| Byco N SD Hydrolyzed Fish Gelatin | 10.0 | 10.0 |
| Citric Acid Monohydrate | 2.0 | 2.0 |
| Pluronic F68 | 2.0 | 2.0 |
|  | 100.0 | 100.0 |

PVP and Fish Gelatin in combination are the secondary film former.

Example 23

| Component | Percent | grams |
| --- | --- | --- |
| HEC | 70.0 | 70.0 |
| PEG 3000 | 30.0 | 30.0 |
|  | 100.0 | 100.0 |

Example 24

| Component | Percent | grams |
| --- | --- | --- |
| HEC | 57.4 | 57.4 |
| PVP | 25.6 | 25.6 |
| Lycasin | 5.0 | 5.0 |
| Pluronic F68 | 10.0 | 10.0 |
| Citric Acid Monohydrate | 2.0 | 2.0 |
|  | 100.0 | 100.0 |

Example 25

| Component | Percent | grams |
| --- | --- | --- |
| HEC | 55.4 | 55.4 |
| PVP | 25.6 | 25.6 |
| Lycasin | 5.0 | 5.0 |
| Pluronic F68 | 4.0 | 4.0 |
| Citric Acid Monohydrate | 10.0 | 10.0 |
|  | 100.0 | 100.0 |

Example 26

| Component | Percent | grams |
| --- | --- | --- |
| Byco M Spray-Dried Hydrolyzed Fish Gelatin | 54.5 | 54.5 |
| NaCMC | 26.0 | 26.0 |
| Soya Lecithin | 7.5 | 7.5 |
| Vanillin | 2.0 | 2.0 |
| Citric Acid Monohydrate | 10.0 | 10.0 |
|  | 100.0 | 100.0 |

Example 27

| Component | Percent | grams |
| --- | --- | --- |
| Byco M Spray-Dried Hydrolyzed Fish Gelatin | 52.0 | 52.0 |
| NaCMC | 24.0 | 24.0 |
| Soya Lecithin | 20.0 | 20.0 |
| Vanillin | 2.0 | 2.0 |
| Citric Acid Monohydrate | 2.0 | 2.0 |
|  | 100.0 | 100.0 |

Example 28

| Component | Percent | grams |
| --- | --- | --- |
| HEC | 63.4 | 63.4 |
| PVP | 25.6 | 25.6 |
| Lycasin | 5.0 | 5.0 |
| Pluronic F68 | 4.0 | 4.0 |
| Citric Acid Monohydrate | 2.0 | 2.0 |
|  | 100.0 | 100.0 |

Example 29

| Component | Percent | grams |
|---|---|---|
| Byco M Spray-Dried Hydrolyzed Fish Gelatin | 68.5 | 68.5 |
| PVP | 20.0 | 20.0 |
| Soya Lecithin | 7.5 | 7.5 |
| Citric Acid Monohydrate | 2.0 | 2.0 |
| Vanillin | 2.0 | 2.0 |
| | 100.0 | 100.0 |

Example 30

| Component | Percent | grams |
|---|---|---|
| Byco M Spray-Dried Hydrolyzed Fish Gelatin | 40.0 | 40.0 |
| HEC | 40.0 | 40.0 |
| Soya Lecithin | 20.0 | 20.0 |
| | 100.0 | 100.0 |

Example 31

| Component | Percent | grams |
|---|---|---|
| HEC | 65.0 | 65.0 |
| NaCMC | 25.0 | 25.0 |
| Soya Lecithin | 10.0 | 10.0 |
| | 100.0 | 100.0 |

Example 32

A dry coating composition having the following formula is made using the procedure of Example 1:

| Component | Percent | grams |
|---|---|---|
| HEC | 54.0 | 54.0 |
| PVP | 25.0 | 25.0 |
| Polydextrose | 12.0 | 12.0 |
| Lycasin | 5.0 | 5.0 |
| Pluronic F68 | 4.0 | 4.0 |
| | 100.0 | 100.0 |

Polydextrose is Litesse supplied by Cultor and is functioning as a secondary film former in combination with polyvinylpyrrolidone (PVP). Fifty grams of the dry coating compostion is dispersed in 950 grams of ambient water using the procedure of Example 1 to create an aqueous coating suspension having a 5.0% solids content. A 1.0 kilogram charge of 500 mg Acetaminophen caplets, which have been previously coated with a theoretical 3.0% weight gain of a pigmented film coating made from an Opadry® II coating composition, as explained in Example 1, are spray-coated with the inventive aqueous coating suspension of this example using the coating procedure of Example 7. Gloss units attained were 225 gu.

Example 33

A dry coating composition having the following formula is made using the procedure of Example 1:

| Component | Percent | grams |
|---|---|---|
| Byco M Spray-Dried Hydrolyzed Fish Gelatin | 55.0 | 1375.0 |
| NaCMC | 27.0 | 675.0 |
| PGA | 10.0 | 250.0 |
| Soya Lecithin | 5.0 | 125.0 |
| Citric Acid Monohydrate | 2.0 | 50.0 |
| Polysorbate 80 | 1.0 | 25.0 |
| | 100.0 | 2500.0 |

2200 grams of the dry coating composition is dispersed in 41.8 kilograms of ambient water using the procedure of Example 1 to create an aqueous coating suspension having a 5.0% solids content.

A 40.0 kilogram charge of 500 mg Acetaminophen caplets, which have been previously coated at a theoretical 3.0% weight gain with a coating made from a pigmented Opadry®II coating composition manufactured by Colorcon, is loaded into a 30" O'Hara Labcoat II coating pan with 4 mixing baffles and 6 anti-slide bars. The aqueous coating suspension is sprayed onto the tablet bed using 2 Schlick Guns, Model 930-33/7-1, with 1.2 mm spray nozzles and 3.0 mm air caps; and a Masterflex digital console peristaltic pump equipped with two 7518-02 pumpheads. During the coating procedure, the atomizing air is 50 psi, pattern air is 30 psi, inlet air temperature is 750C, outlet air is 48° C., the tablet bed temperature is at 43°–45° C., the pan speed is 10–12 rpm, and the coating liquid feed rate is 125 g/min. A theoretical 5.0% dry coating weight gain is applied to the tablet charge, producing very smooth, non-tacky, very shiny coated tablets with a gloss reading of 205 g.u.

Example 34

Although finished tablet gloss is much higher by application of a clear formulation of the present invention over a colored subcoat, a colorant may be incorporated into the formulation of the invention, if desired, to eliminate the step of applying a colored subcoat, as illustrated in this example. In this example, a dry coating composition having the following formulation is made using the procedure of Example 1:

| Component | Percent | grams |
|---|---|---|
| HEC | 46.34 | 46.34 |
| PVP | 18.86 | 18.86 |
| Triacetin | 4.10 | 4.10 |
| Pluronic F87 | 1.64 | 1.64 |
| Stearic Acid | 2.06 | 2.06 |
| TiO2 | 24.50 | 24.50 |
| FD&C Blue No. 2 Lake | 2.50 | 2.50 |
| | 100.0 | 100.0 |

Stearic Acid is from Oleotec Ltd., and is the glidant. TiO2 is Titanium Dioxide from Kronos, and FD&C Blue No. 2 Lake is manufactured by Colorcon, West Point, PA.

A coating suspension is made by dispersing 10.5 grams of the dry coating composition of this example into 94.5 grams of purified water to create a suspension having a 10.0% solids context. Coating is performed on a 300 gram mixed charge of aspirins and placebos in an Aeromatic Strea-1 coater as in Example 1, and a theoretical 3.5% weight gain is applied to the tablets. Tablets are smooth, evenly pigmented, and of suitable shine with a gloss measurement of 148 gloss units.

Example 35

Example 34 is repeated, except the following formulation is used:

| Component | Percent | grams |
|---|---|---|
| HEC | 56.5 | 56.5 |
| PVP | 23.0 | 23.0 |
| Triacetin | 5.0 | 5.0 |
| Citric Acid Monohydrate | 2.0 | 2.0 |
| Stearic Acid | 2.5 | 2.5 |
| Talc | 10.0 | 10.0 |
| D&C Yellow No. 10 Dye | 1.0 | 1.0 |
| | 100.0 | 100.0 |

D&C Yellow No. 10 dye is manufactured by Hilton Davis. Talc is Altalc 400 from Whittaker, Clark and Daniels and serves a dual role as glidant and opacifier in the formula. Gloss measurement of the tablets was 152 g.u.

Example 36

This example illustrates the use of a liquid color premix as the colorant for coloring the inventive film coating. In this example, the dry coating composition of Example 28 is prepared and then mixed into water using the procedure of Example 7 to form a coating suspension having a 5% solids content. 950 grams of this suspension is then placed into an empty vessel, and 12.5 grams of an Opatint® (DD11000 (green)) liquid color dispersion (containing 20% dry solids) (a liquid color premix), manufactured by Colorcon, is added and mixed into the suspension producing a colored suspension having a total dry solids weight of 50.0 grams in the colored suspension. The percentage of inventive coating suspension to color is at a ratio of 95:5.

A 1.0 kilogram charge of uncoated 11 mm deep convex placebos is loaded into a 12" O'Hara coating pan and the colored coating suspension prepared as stated above is spray-coated using the procedure of Example 7. A theoretical 5.0% dry coating weight gain is applied to the tablets producing very elegant, glossy tablets with a gloss measurement of 196 g.u.

Example 37

The dry coating composition of Example 7 is prepared and then mixed into water using the procedure of Example 6 to form a coating suspension. This coating suspension then is applied by spray-coating in a 15" O'Hara coating pan using the procedure of Example 6 onto a 3.0 kilogram charge of uncoated 200 mg Ibuprofen cores. A theoretical 5.0% dry coating weight gain is applied to the tablets, producing very smooth, non-tacky, very shiny coated tablets registering 173 g.u.

Example 38

The dry coating composition of Example 7 is prepared and then mixed into water using the procedure of Example 6 to from a coating suspension. This coating suspension then is applied by spray-coating in a 15" O'Hara coating pan using the procedure of Example 6 onto a 3.0 kilogram charge of uncoated 500 mg Acetaminophen caplets. A 5% dry coating weight gain is applied to the caplets, and the coated caplets are very elegant with a gloss measurement of 191 g.u. Then using a Hartnett Delta printer coated caplets of this example are printed with a white Opacode® ink, formulation S-1-7090, an alcohol-based printing ink manufactured by Colorcon, West Point Pa. The ink transferred to the coated tablets completely, with excellent adhesion.

Example 39

The dry coating composition of Example 6 is prepared and then mixed into water following the procedure of Example 6 to from an aqueous coating suspension. A 3.0 kilogram charge of ⅜" diameter placebos which have been previously coated with a coating made from a red Opadry® II coating composition, manufactured by Colorcon, is spray-coated with the coating suspension of this example in a 15" O'Hara Labcoat II pan with 4 mixing baffles and 6 anti-slide bars. Two Schlick Spray guns Model #931/7-1 S22 are used to deliver the coating suspension through a Masterflex digital console peristaltic pump with 2 7518-02 pumpheads. During the coating procedure, the atomizing air is 30 psi, pattern air is 35 psi, inlet air temperature is 65° C., outlet air is 44° C., the tablet bed temperature is 41° C., pan speed is 18 rpm, the coating liquid feed rate is 30 g/min, and the total coating time is 1 hour and 50 minutes. A 5% dry coating weight gain is applied to the tablets, and the coated tablets are non-tacky, extremely smooth, and glossy with a gloss reading of 218 g.u.

Example 40

The inventive dry coating compositions may be used to create aqueous coating suspensions that are applied to substrates, such as pharmaceutical substrates, by dipping or enrobing, as illustrated in this example. In this example, the a dry coating composition of Example 6 is prepared and then mixed into water following the procedure of Example 1 to form 5.0% solids aqueous coating suspension. The suspension is allowed to deaerate to remove any bubbles. Aspirin tablets, which have been previously coated with a 3.0% weight gain of a pigmented film coating made from an Opadry® II coating composition, formula Y-22-15118 (red), manufactured by Colorcon, West Point PA, are individually dipped into the coating suspension by using a pair of forceps. Excess coating is removed by shaking each tablet after dipping. Coated tablets are then slowly rotated by hand under a forced air dryer for 1 to 2 minutes until the coating sets slightly, and then the tablets are placed in a plastic weigh boat under the air dryer to dry for an additional 15 minutes. After drying, tablets are visually inspected for film-coat quality and gloss measurement. The coated tablets of this example are exceptionally glossy and smooth, reflective, bright and elegant looking. The gloss measurement readings are 233 g.u.

Example 41

The dry film coating composition of Example 28 is made using the procedure of Example 1, and the coating composition is mixed into water using the procedure of Example 1 to form an aqueous coating suspension having a 15% solids content. Aspirin tablets, having a previously applied coating (a subcoat), are dipped into the suspension following the procedure of Example 40 to form an inventive coating on the tablet over the subcoat. The resultant tablets are elegant looking, and exceptionally glossy and smooth. The gloss measurement attained is 243 g.u.

Example 42

Fish gelatin is dispersed in ambient water to produce a clear solution having a 20% solids content. The solution is allowed to deaerate to remove any bubbles. Aspirin tablets, having a previously applied subcoat, are dipped into the suspension following the procedure of Example 40 to form an inventive coating on the tablets over the subcoat. The resultant coated tablets are exceptionally glossy and smooth, reflective, bright and elegant looking. The gloss measurement readings are 237 g.u.

Example 43

Hydroxy ethyl cellulose is dispersed in ambient water to produce a clear solution having a 10% solids content. The solution is allowed to deaerate to remove any bubbles. Aspirin tablets, having a previously applied subcoat, are dipped into the suspension following the procedure of Example 40 to form an inventive coating on the tablets over the subcoat. The resultant coated tablets are elegant looking, and exceptionally glossy and smooth. The gloss measurement attained is 202 g.u.

ADVANTAGES

In accordance with our invention, film coating suspensions may be spray-coated onto tablets and the like at weight gains substantially higher than 1.0% to produce film coatings having an exceptional shine and smoothness not achieved with the inventions of the aforementioned patents. Moreover, our coatings do not have a frost-like or hazy appearance.

In accordance with our invention, a coating is produced that has a finished product gloss and smoothness comparable to the current commercially marketed medicaments that are gel-dipped or enrobed and/or sugar-coated.

Clear (non-pigmented) inventive coatings may be applied to tablets and the like as an overcoat to a substrate previously coated with a pigmented aqueous coating. Also, clear coatings made in accordance with the invention may be used as a stand alone clear coating for a non-pigmented, non-coated substrate.

Non-clear coatings (coating having pigments and/or colorants) made in accordance with the invention, as well as the inventive clear coatings, have a smooth and glossy appearance.

Another advantage of the present invention is the exceptional slip afforded the tablets after coating. The tablets slide off one another, contributing to ease of packaging and ease of swallowing for the consumer.

However, the slick surface of the finished tablet product is not deleterious to printing.

A further advantage of the present invention is that the inventive coating may be applied to tablets and the like by using traditional spray-coating equipment, traditional spray-coating equipment conditions, and room temperature mixing conditions, which represents substantial time-savings and substantial labor-savings in processing over traditional gel-dipping processes, traditional sugar-coating processes, and processes like that of Shen U.S. Pat. No. 5,683,717.

What is claimed is:

1. A dry film coating composition for forming a coating suspension for film coating pharmaceuticals, food, confectionery forms, and agricultural seeds, consisting essentially of (1) a primary film former, the primary film former comprising low bloom strength gelatin, or hydroxyethyl cellulose, or a combination thereof, and (2) a secondary film former, or a plasticizer, or a surfactant, or a glidant, or a suspension aid, or a colorant, or a flavorant, or a combination thereof.

2. The composition of claim 1, the gelatin being fish gelatin.

3. The composition of claim 1, the primary film former being in a range of 45% to 90% by weight of the composition.

4. The composition of claim 1, the primary film former being in a range of 45% to 75% by weight of the composition.

5. The composition of claim 1, the primary film former being in a range of 50% to 65% by weight of the composition.

6. The composition of claim 1, the secondary film former being in a range of greater than 0% to 50% by weight of the composition.

7. The composition of claim 1 the secondary film former being in a range of 5% to 45% by weight of the composition.

8. The composition of claim 1, the secondary film former being in a range of 20% to 40% by weight of the composition.

9. The composition of claim 1, the plasticizer being in a range of greater than 0% to 30% by weight of the composition.

10. The composition of claim 1, the plasticizer being in a range of 1% to 15% by weight of the composition.

11. The composition of claim 1, the plasticizer being in a range of 4% to 10% by weight of the composition.

12. The composition of claim 1, the surfactant being in a range of greater than 0% to 20% by weight of the composition.

13. The composition of claim 1, the surfactant being in a range of 1% to 10% by weight of the composition.

14. The composition of claim 1, the glidant being in a range of greater than 0% to 13% by weight of the composition.

15. The composition of claim 1, the glidant being in a range of 0.5% to 5% by weight of the composition.

16. The composition of claim 1, the suspension aid being in a range of greater than 0% to 15% by weight of the composition.

17. The composition of claim 1, the suspension aid being in a range of 2% to 12% by weight of the composition.

18. The composition of claim 1, the colorant being in a range of greater than 0% to 27% by weight of the composition.

19. The composition of claim 1, the colorant being in a range of 1% to 16% by weight of the composition.

20. The composition of claim 1, the flavorant being in a range of greater than 0% to 12% by weight of the composition.

21. The composition of claim 1,
the flavorant being in a range of 1% to 6% by weight of the composition.

22. A dry film coating composition for forming a coating suspension for film coating pharmaceuticals, food, confectionery forms, and agricultural seeds, consisting essentially of
low bloom strength fish gelatin in a range of 50% to 65% by weight of the composition,
a secondary film former in a range of 20% to about 40% by weight of the composition,
a surfactant in a range of 1% to 10% by weight of the composition,
a suspension aid in a range of 2–12% by weight of the composition, and
a flavorant in a range of 1% to 6% by weight of the composition,
the secondary film former being sodium alginate, sodium carboxymethlylcellulose, pectin, gelatin, propylene glycol alginate, metlhylcellitlose, polydextrose, polyvinypylTolidone, or combinations thereof,
the surfactant being soya lecithin, sodium lauryl sulfate, polysorbate 80, polyoxyethylene polypropylene block copolymers, or combinations thereof,
the suspension aid being xanthan gum, propylene glycol alginate, pectin, or combinations thereof, and
the flavorant being vanillin, sodium citrate, citric acid, mint, orange, lemon oil, or combinations thereof.

23. A dry film coating composition for forming a coating suspension for film coating pharmaceuticals, food, confectionery forms, and agricultural seeds, consisting essentially of
hydroxyethyl cellulose being in a range of 50% to 65% by weight of the composition,
a secondary film former being in a range of 20% to 40% by weight of the composition,
a plasticizer being in a range of 4% to 10% by weight of the composition,
a surfactant being in a range of 1% to 10% by weight of the composition, and
a flavorant being in a range of 1% to 6% by weight of the composition,
the secondary film former being sodium alginate, sodium carboxymethylccllulose, pectin, gelatin, propylene glycol alginate, methylccllulose, polydextrose, polyvinypyrrolidonc, or combinations thereof,
the plasticizer being glycerin, maltitol solution, propylene glycol, polyethylene glycol, triethyl citrate, glyceryl triacetate, or combinations thereof,
the surfactant being soya lecithin, sodium lauryl sulfate, polysorbate 80, polyoxyetlhylene polyoxypropylene block copolymers, or combinations thereof and
the flavorant being vanillin, sodium citrate, citric acid, mint, orange, lemon oil, or combinations thereof.

24. A method of coating pharmaceutical substrates, food substrates, confectionery form substrates, or agricultural seed substrates with a high gloss film coating, consisting essentially of the steps of
preparing a coating suspension consisting essentially of fish gelatin and water,
applying an effective amount of the coating suspension onto said substrates to form a film coating on said substrates, and
drying the film coating on said substrates.

25. The method of claim 24, further including the step of applying a colored subcoat onto the substrate prior to applying the coating suspension.

26. The method of claim 24,
the amount of coating suspension applied to the substrates resulting in weight gains to the substrates of greater than 1% by dry weight basis.

27. The method of claim 24,
the amount of coating suspension applied to the substrates resulting in weight gains to the substrates of 3% or above by dry weight basis.

28. The method of claim 24,
the amount of coating suspension applied to the substrates resulting in weight gains to the substrates of 5% or above by dry weight basis.

29. A method of coating pharmaceutical substrates, food substrates, confectionery form substrates, or agricultural seed substrates with a high gloss film coating, consisting essentially of the steps of
mixing (1) a primary film former, the primary film former consisting essentially of low bloom strength gelatin, or hydroxyethyl cellulose, or combination thereof, and (2) a secondary film former, or a plasticizer, or a surfactant, or a glidant, or a suspension aid, or a colorant, or a flavorant, or a combination thereof, into water to form a coating suspension,
applying an effective amount of the coating suspension onto said substrates to form a film coating on said substrates, and
drying the film coating on said substrates.

30. The method of claim 29, further including the step of applying a colored subcoat onto the substrates prior to applying the coating suspension.

31. The method of claim 29,
the amount of coating suspension applied to the substrates resulting in weight gains to the substrates of greater than 1% by dry weight basis.

32. The method of claim 29,
the amount of coating suspension applied to the substrates resulting in the weight gains to the substrates of 3% or above by dry weight basis.

33. The method of claim 29,
the amount of coating suspension applied to the substrates resulting in weight gains to the substrates of 5% or above by dry weight basis.

34. The method of claim 29,
the gelatin being fish gelatin.

35. The method of claim 29,
the primary film former being in a range of 45% to 90% by weight of the non-water ingredients of the coating suspension.

36. The method of claim 29,
the primary film former being in a range of 45% to 75% by weight of the non-water ingredients of the coating suspension.

37. The method of claim 29,
the primary film former being in a range of 50% to 65% by weight of the non-water ingredients of the coating suspension.

38. The method of claim 29,
the secondary film former being in a range of greater than 0% to 50% by weight of the non-water ingredients of the coating suspension.

39. The method of claim 29,
the secondary film former being in a range of 5% to 45% by weight of the non-water ingredients of the coating suspension.
40. The method of claim 29,
the secondary film former being in a range of 20% to 40% by weight of the non-water ingredients of the coating suspension.
41. The method of claim 29,
the plasticizer being in a range of greater than 0% to 30% by weight of the non-water ingredients of the coating suspension.
42. The method of claim 29,
the plasticizer being in a range of 1% to 15% by weight of the non-water ingredients of the coating suspension.
43. The method of claim 29,
the plasticizer being in a range of 4% to 10% by weight of the non-water ingredients of the coating suspension.
44. The method of claim 29,
the surfactant being in a range of greater than 0% to 20% by weight of the non-water ingredients of the coating suspension.
45. The method of claim 29,
the surfactant being in a range of 1% to 10% by weight of the non-water ingredients of the coating suspension.
46. The method of claim 29,
the glidant being in a range of greater than 0% to 13% by weight of the non-water ingredients of the coating suspension.
47. The method of claim 29,
the glidant being in a range of 0.5% to 5% by weight of the non-water ingredients of the coating suspension.
48. The method of claim 29,
the suspension aid being in a range of greater than 0% to 15% by weight of the non-water ingredients of the coating suspension.
49. The method of claim 29,
the suspension aid being in a range of 2% to 12% by weight of the non-water ingredients of the coating suspension.
50. The method of claim 29,
the colorant being in a range of greater than 0% to 27% by weight of the non-water ingredients of the coating suspension.
51. The method of claim 29,
the colorant being in a range of 1% to 16% by weight of the non-water ingredients of the coating suspension.
52. The method of claim 29,
the flavorant being in a range of greater than 0% to 12% by weight of the non-water ingredients of the coating suspension.
53. The method of claim 29,
the flavorant being in a range of 1% to 6% by weight of the non-water ingredients of the coating suspension.
54. An aqueous coating suspension for film coating pharmaceuticals, food, confectionery forms, and agricultural seeds, consisting essentially of
(1) a primary film former, the primary film former comprising low bloom strength gelatin or low bloom strength gelatin and hydroxyethyl cellulose, and
(2) a secondary film former, or a plasticizer, or a surfactant, or a glidant, or a suspension aid, or a colorant, or a flavorant, or a combination thereof, and
(3) water.
55. The suspension of claim 54,
the gelatin being fish gelatin.
56. The suspension of claim 54,
the primary film former being in a range of 45% to 90% of the non-water ingredients of the suspension.
57. The suspension of claim 54,
the primary film former being in a range of 45% to 75% of the non-water ingredients of the suspension.
58. The suspension of claim 54.,
the primary film former being in a range of 50% to 65% of the non-water ingredients of the suspension.
59. The suspension of claim 54,
the secondary film former being in a range of greater than 0% to 50% of the non-water ingredients of the suspension.
60. The suspension of claim 54,
the secondary film former being in a range of 5% to 45% of the non-water ingredients of the suspension.
61. The suspension of claim 54,
the secondary film former being in a range of 20% to 40% of the non-water ingredients of the suspension.
62. The suspension of claim 54,
the plasticizer being in a range of greater than 0% to 30% of the non-water ingredients of the suspension.
63. The suspension of claim 54,
the plasticizer being in a range of 1% to 15% of the non-water ingredients of the suspension.
64. The suspension of claim 54,
the plasticizer being in a range of 4% to 10% of the non-water ingredients of the suspension.
65. The suspension of claim 54,
the surfactant being in a range of greater than 0% to 20% of the non-water ingredients of the suspension.
66. The suspension of claim 54,
the surfactant being in a range of 1% to 6% of the non-water ingredients of the suspension.
67. The suspension of claim 54,
the glidant being in a range of greater than 0% to 13% of the non-water ingredients of the suspension.
68. The suspension of claim 54,
the glidant being in a range of 0.5% to 5% of the non-water ingredients of the suspension.
69. The suspension of claim 54,
the suspension aid being in a range of greater than 0% to 15% of the non-water ingredients of the suspension.
70. The suspension of claim 54,,
the suspension aid being in a range of 2% to 12% of the non-water ingredients of the suspension.
71. The suspension of claim 54,
the colorant being in a range of greater than 0% to 27% of the non-water ingredients of the suspension.
72. The suspension of claim 54,
the colorant being in a range of 1% to 16% of the non-water ingredients of the suspension.
73. The suspension of claim 54,
the flavorant being in a range of greater than 0% to 12% of the non-water ingredients of the suspension.
74. The suspension of claim 54,
the flavorant being in a range of 1% to 6% of the non-water ingredients of the suspension.
75. A method of coating pharmaceutical substrates, food substrates, confectionery form substrates, or agricultural seed substrates with a high gloss film coating, consisting essentially of the steps of preparing a coating suspension consisting essentially of hydroxyethyl cellulose and water, applying an effective amount of the coating suspension onto said substrates to form a film coating on said substrates, and drying the film coating on said substrates.

76. A method of coating pharmaceutical substrates, food substrates, confectionery form substrates, or agricultural seed substrates with a high gloss film coating, consisting essentially of the steps of preparing a coating suspension consisting essentially of low bloom gelatin, hydroxyethyl cellulose, and water, applying an effective amount of the coating suspension onto said substrates to form a film coating on said substrates, and drying the film coating on said substrates.

77. The film coating composition of claim 29, wherein the coating suspension is applied onto said substrates using traditional spray-coating equipment and traditional spray-coating equipment conditions.

78. A method of coating pharmaceutical substrates, food substrates, confectionery form substrates, or agricultural seed substrates with a high gloss film coating, consisting essentially of the steps of mixing (1) a primary film former, the primary film former consisting essentially of low bloom strength gelatin, hydroxyethyl cellulose, or a combination thereof, and (2) a secondary film former, or a plasticizer, or a surfactant, or a glidant, or a suspension aid, or a flavorant, or a combination thereof, into water to form a coating suspension, applying an effective amount of the coating suspension onto said substrates to form a film coating on said substrates, and drying the film coating on said substrates, the film coating having a high gloss without a frost-like appearance.

79. A method of coating pharmaceutical substrates, food substrates, confectionery form substrates, or agricultural seed substrates with a high gloss film coating, consisting essentially of the steps of mixing (1) a primary film former, the primary film former consisting essentially of low bloom strength gelatin, and (2) a secondary film former, or a plasticizer, or a surfactant, or a glidant, or a suspension aid, or a colorant, or a flavorant, or a combination thereof, into water to form a coating suspension, applying an effective amount of the coating suspension onto said substrates to form a film coating on said substrates, and drying the film coating on said substrates.

80. A method of coating pharmaceutical substrates, food substrates, confectionery form substrates, and agricultural seed substrates with a high gloss film coating, consisting essentially of the steps of mixing (1) a primary film former, the primary film former consisting essentially of hydroxyethyl cellulose, and (2) a secondary film former, or a plasticizer, or a surfactant, or a glidant, or a suspension aid, or a colorant, or a flavorant, or a combination thereof, into water to form a coating suspension, applying an effective amount of the coating suspension onto said substrates to form a film coating on said substrates, and drying the film coating on said substrates.

81. A method of coating pharmaceutical substrates, food substrates, confectionery form substrates, and agricultural seed substrates with a high gloss film coating, consisting essentially of the steps of mixing (1) a primary film former, the primary film former consisting essentially of low bloom strength gelatin and hydroxyethyl cellulose, and (2) a secondary film former, or a plasticizer, or a surfactant, or a glidant, or a suspension aid, or a colorant, or a flavorant, or a combination thereof, into water to form a coating suspension, applying an effective amount of the coating suspension onto said substrates to form a film coating on said substrates, and drying the film coating on said substrates.

* * * * *